(12) United States Patent  
Kobayashi et al.

(10) Patent No.: US 6,740,106 B2  
(45) Date of Patent: May 25, 2004

(54) FORCEPS FOR ENDOSCOPE AND MANUFACTURING METHOD OF FORCEPS

(75) Inventors: Hiroshi Kobayashi, Omiya (JP); Yasuo Akiba, Omiya (JP); Shigeo Konno, Omiya (JP); Masao Ide, Omiya (JP)

(73) Assignee: Fuji Photo Optical Co., Ltd., Omiya (JP)

( * ) Notice: Subject to any disclaimer, the term of this patent is extended or adjusted under 35 U.S.C. 154(b) by 0 days.

(21) Appl. No.: 09/817,440

(22) Filed: Mar. 27, 2001

(65) Prior Publication Data

US 2001/0025149 A1 Sep. 27, 2001

(30) Foreign Application Priority Data

Mar. 27, 2000 (JP) .......................... 2000-086811

(51) Int. Cl.⁷ .............................................. A61B 17/28
(52) U.S. Cl. ..................................................... 606/205
(58) Field of Search ......................... 606/52, 205, 207, 606/208, 210, 45, 46, 206

(56) References Cited

U.S. PATENT DOCUMENTS 4,492,231 A * 1/1985 Auth ............................ 606/40
5,196,009 A * 3/1993 Kirwan, Jr. ................... 606/51
5,695,510 A * 12/1997 Hood ........................... 606/169
5,746,740 A * 5/1998 Nicholas ....................... 606/205

FOREIGN PATENT DOCUMENTS

| DE | 689 13 909 T2 | 10/1994 |
| EP | 0 367 818 B1 | 3/1994 |
| JP | 5990553 | 5/1984 |
| JP | 61128954 | 6/1986 |
| JP | 3-51537 A | 3/1991 |

* cited by examiner

Primary Examiner—Danny Worrell  
(74) Attorney, Agent, or Firm—Birch, Stewart, Kolasch & Birch, LLP (57) ABSTRACT

An electroless nickel plating film layer is formed over a surface of a base material of a forceps piece made of austenitic stainless steel. The forceps are chemical resistant. The electroless nickel plating film layer displays a hardness suitable for the forceps and superior toughness, and allows an edge to be put on the electroless nickel plating film layer more easily than a hardened steel that has the same hardness.

12 Claims, 8 Drawing Sheets

FORCEPS FOR ENDOSCOPE AND MANUFACTURING METHOD OF FORCEPS

BACKGROUND OF THE INVENTION

1. Field of the Invention

The present invention relates to biopsy forceps and scissors forceps with blades, which an endoscope is equipped with for removing a piece of tissue from an inner part of a body, and a manufacturing method of the forceps.

2. Description of Related Art

A biopsy forceps is used to remove a piece of tissue from an inner part of a body by being inserted into the inner part of the body through a treatment tool insertion opening of an endoscope (e.g. Japanese Patent Application Laid-open Nos. 59-90553 and 61-128954).

A base material of pieces of the biopsy forceps is conventionally made of martensitic stainless steel or austenitic stainless steel. The forceps piece made of martensitic stainless steel is hardened by a heat process, and has a superior ability as a blade. However, in view of chemical resistance, the forceps piece made of martensitic stainless steel is corroded with acidic chemical, and thus its sharpness is deteriorated quickly and corroded dirt may fall into the body. On the other hand, the forceps piece made of austenitic stainless steel displays superior chemical resistant property (anti-disinfectant). However, the forceps piece made of austenitic stainless steel has insufficient sharpness due to its low hardness.

SUMMARY OF THE INVENTION

The present invention has been developed in view of the above-described circumstances, and has as its object the provision of a forceps for an endoscope and a method for manufacturing the forceps which has good chemical resistance as well as good sharpness.

In order to achieve the above-described object, the present invention is directed to a forceps for an endoscope, the forceps being inserted through a treatment tool insertion opening of the endoscope for treating a part of a body to which the endoscope is inserted, wherein: an electroless nickel plating film layer is formed over a surface of a base material of a piece of the forceps.

Moreover, in order to achieve the above-described object, the present invention is directed to a method for manufacturing a forceps for an endoscope, the forceps being inserted through a treatment tool insertion opening of the endoscope for treating a part of a body to which the endoscope is inserted, the method comprising the steps of: forming an electroless nickel plating film layer over a surface of a base material of a piece of the forceps by electroless plating; and putting an edge on the electroless nickel plating film layer.

According to the forceps for the endoscope of the present invention, the electroless nickel plating film layer is formed over the surface of the base material of the forceps piece; thus, the forceps has a good chemical resistance. Moreover, since the electroless nickel plating film layer has a hardness suitable for the forceps piece and also has superior toughness, an edging process can be easily performed on the electroless nickel plating film layer. Furthermore, by forming a thick electroless nickel plating film layer, re-edging process can be easily performed even in a case where a blade is broken by an external force or where an error in a processed size is corrected; thus the maintenance for the forceps improves. The base material for the forceps piece may be made of martensitic stainless steel or austenitic stainless steel, but if it is made of austenitic stainless steel, the chemical resistant properties still improve greatly.

BRIEF DESCRIPTION OF THE DRAWINGS

The nature of this invention, as well as other objects and advantages thereof, will be explained in the following with reference to the accompanying drawings, in which like reference characters designate the same or similar parts throughout the figures and wherein.

DETAILED DESCRIPTION OF THE PREFERRED EMBODIMENTS

Hereunder a preferred embodiment will be described of a forceps for an endoscope of the present invention in accordance with the accompanying drawings.

Figure 8:
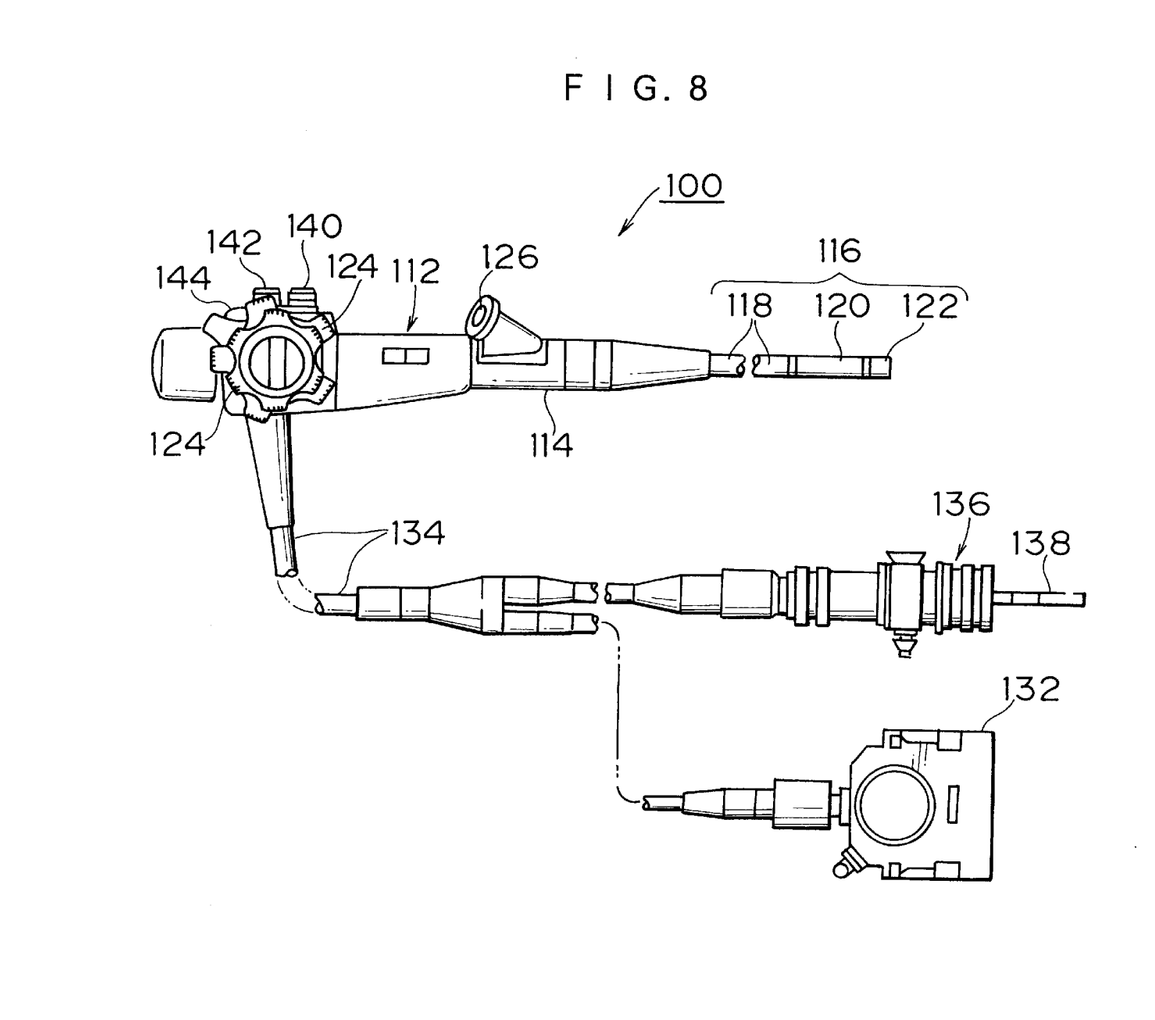
FIG. 8 is a view of the entire endoscope to which the forceps for the endoscope of the present embodiment is applied.

First, an endoscope to which a forceps according to an embodiment of the present invention will be applied is described by referring to FIG. 8. An endoscope 100 in FIG. 8 has a hand control part 112, an insertion part 116, which is connected with a front joint 114 of the hand control part 112, and so forth. The insertion part 116 comprises a soft part 118, a curved part 120, and a hard head part 122, The curved part 120 is connected with a pair of angle control knobs 124, which are provided to the hand control part 112, through angle control wires (not shown), which are inserted through the soft part 118. When the angle control knobs 124 are rotated by the operator, the curved part 120 is curved, and the hard head part 122 is directed to a controlled, that is, a desired, direction. A treatment tool insertion opening 126 is formed at the front joint 114. Treatment tools such as a biopsy forceps and high frequency snare are inserted into the insertion part 116 through the treatment tool insertion opening 126.

A treatment tool channel exit (not shown) is formed at the end face of the hard head part 122. The treatment tool channel exit is connected with the treatment tool insertion opening 126 through a treatment tool channel (not shown). The forceps for the endoscope is inserted into the treatment tool insertion opening 126, is then guided through the treatment tool channel to the treatment tool channel exit, and is projected from the treatment tool channel exit so as to be used.

At the proximity of the treatment tool channel exit, an air supply opening, a water supply opening, an objective lens, an illumination lens, and so forth, all not shown, are provided. An image of an observed subject is formed by the objective lens and is captured by an image capturing device (not shown) to be converted into an image signal. Then, the signal is processed by a processor (not shown) to which an electric connector 132 is connected, and is displayed on a monitor (not shown).

A light guide (not shown) is provided at the rear of the illumination lens. The light guide is inserted through the curved part 120, the soft part 118, the hand control part 112 and a soft cable 134, and is connected with a light guide bar 138 of a light guide connector 136, which is connected with the soft cable 134. When the light guide bar 138 is connected with a light source device (not shown), the light from the light source device is projected to the subject through the light guide and the illumination lens.

The hand control part 112 is provided also with an air/water supply valve 140, at the proximity of which a suction valve 142 and a shutter button 144 are arranged.

Figure 1:
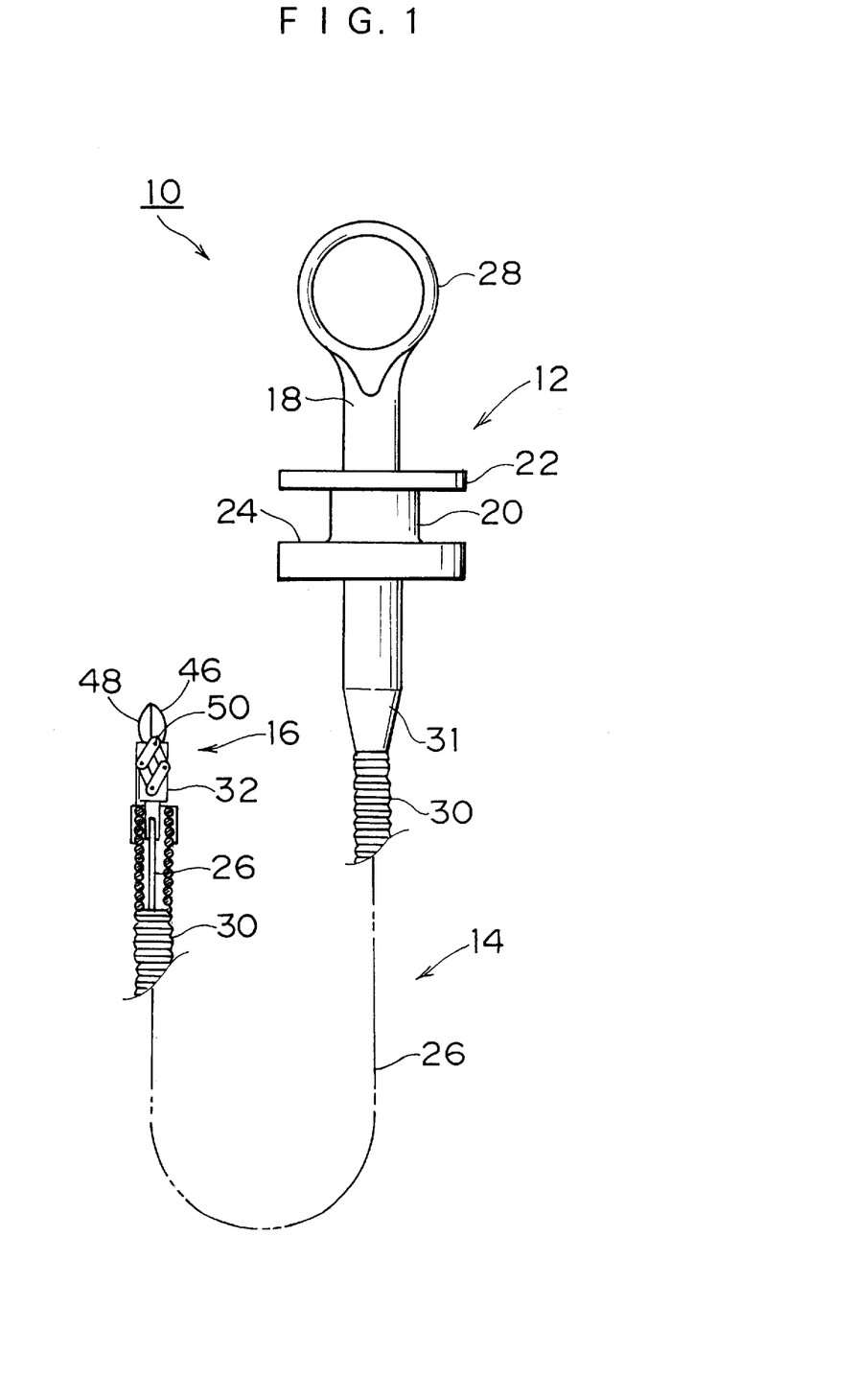
FIG. 1 is a view of an entire biopsy forceps of the present embodiment.

FIG. 1 is a front view of a biopsy forceps 10 according to an embodiment of the present invention. The biopsy forceps 10 in FIG. 1 comprises a hand control part 12, an insertion part 14, which is inserted into the treatment tool insertion opening of the endoscope, and a forceps part 16.

The hand control part 12 is provided with an axial body 18, which is slidably inserted into a cylindrical control element 20. Flanges 22 and 24 are formed at the top (rear) and bottom (front) ends of the control element 20, respectively. The control element 20 is connected with a slider (not shown), which is slidably arranged inside the axial body 18, with a screw (not shown). The rear end of a control wire 26 is fixed to the slider, and the forceps part 16 is connected with the front end of the control wire 26.

At the top (rear) end of the axial body 18, a finger hook 28 is formed, through which the thumb of the operator is inserted in operation. In this state, the index finger and the middle finger are inserted between the flange 22 and the flange 24, and the control element 20 is then controlled by pushing or pulling. When the control element 20 is operated, the forceps part 16 connected through the slider and the control wire 26 is moved.

The insertion part 14 is formed with an elastic secure coil spring 30, the top (rear) end of which is connected with the bottom (front) end of the axial body 18 through a bending prevention tube 31. The control wire 26 is inserted through the inside of the secure coil spring 30, and the front end of the secure coil spring 30 is connected with a substantially cylindrical forceps body 32 of the forceps part 16.

Figure 2:
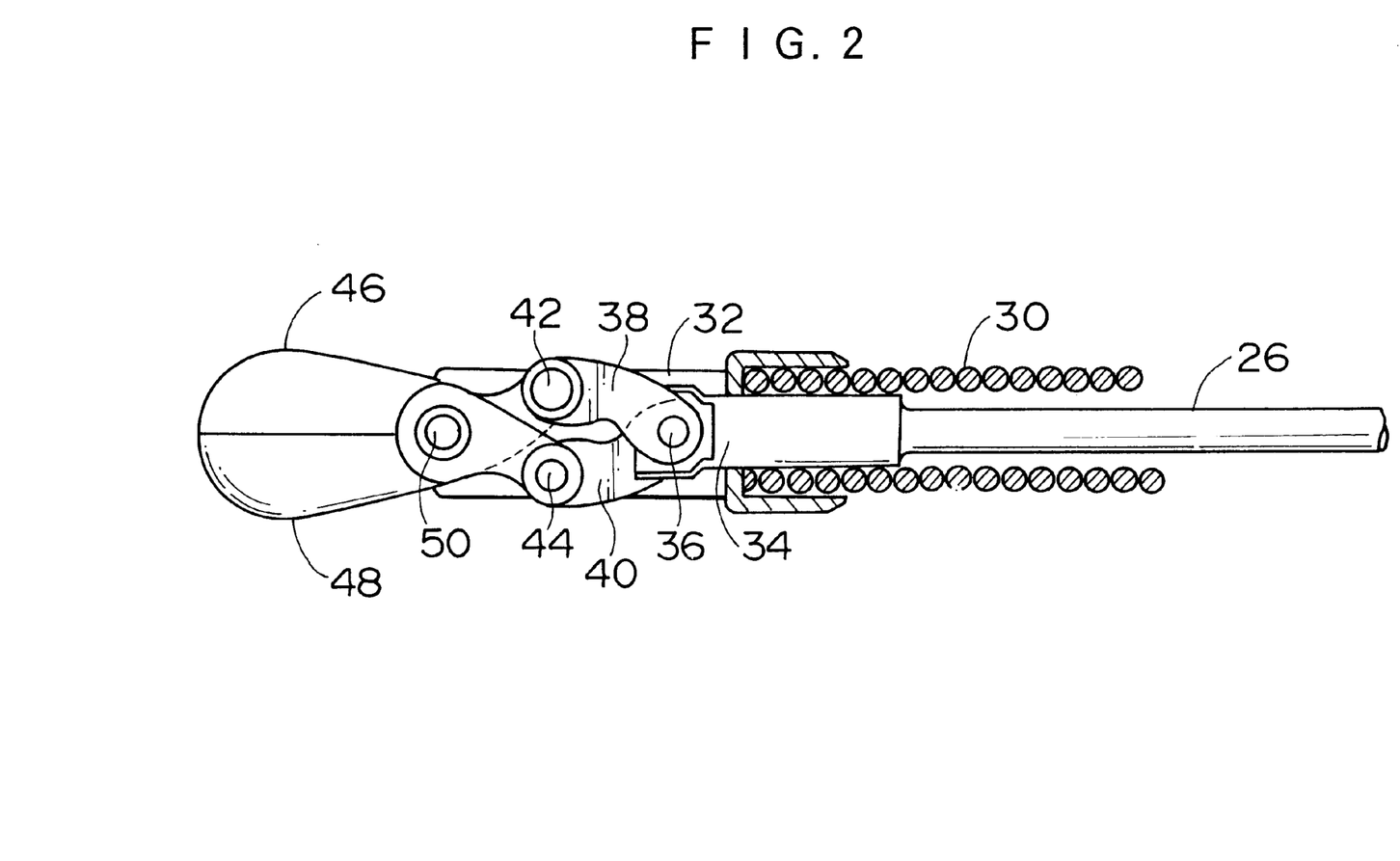
FIG. 2 is an enlarged view showing a structure of a forceps part of the biopsy forceps in FIG. 1.
Figure 3:
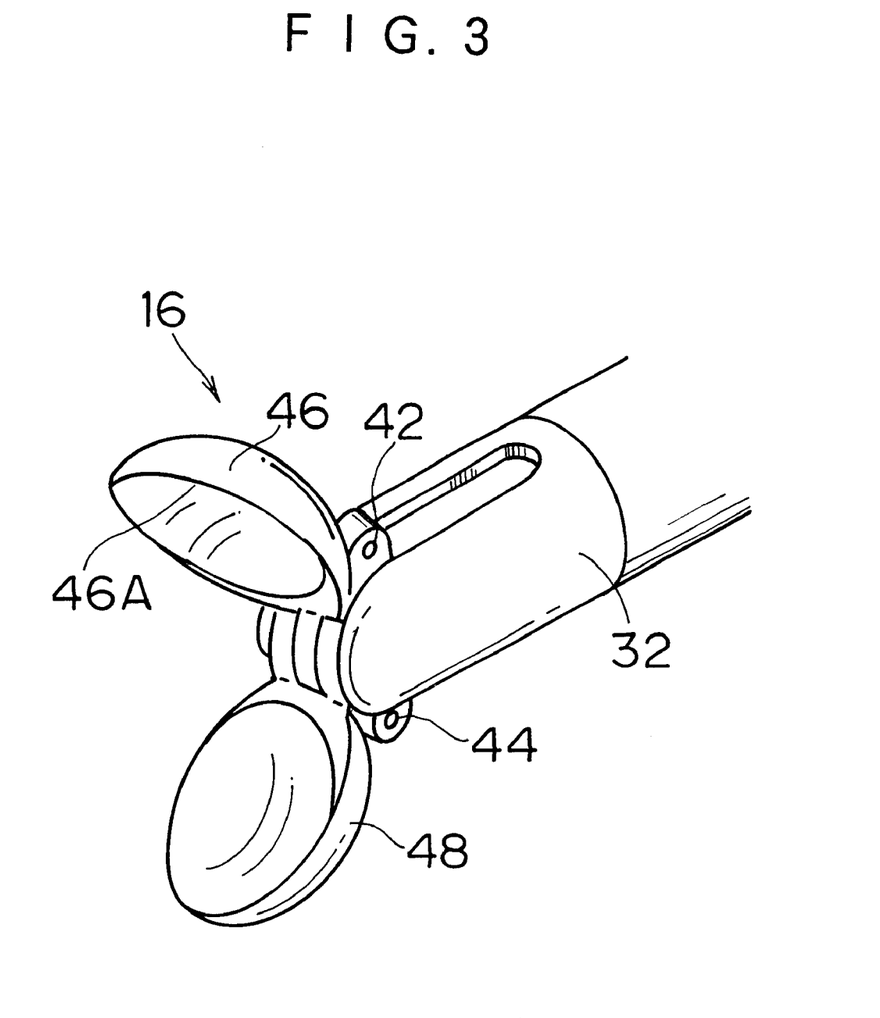
FIG. 3 is a perspective view showing a state where the forceps piece of the forceps part in FIG. 2 is opened.

As seen from FIG. 2, the forceps part 16 has a connecting block 34, which is connected with the front end of the control wire 26. Ends of links 38 and 40 are rotatably supported by a pin 36 on the connecting block 34. The other ends of the links 38 and 40 are connected with forceps pieces 48 and 46 through pins 42 and 44, respectively. At overlapping parts, the forceps pieces 46 and 48 are rotatably supported by a pin 50 on the forceps body 32. Thus, when the control element 20 in FIG. 1 is moved up or down and the control wire 26 is pulled out or pushed in, the forceps pieces 46 and 48 are rotated about the pin 50 in FIG. 2 in opposite directions, and are closed or opened as shown in FIGS. 2 and 3.

A method for manufacturing the forceps pieces 46 and 48 in the present embodiment will be described. In the description, a method for manufacturing the forceps piece 48 is the same as that of the forceps piece 46; thus the method for manufacturing the forceps piece 46 only will be described, and that of the forceps piece 48 is omitted.

Base material of the forceps piece 46 is made of austenitic stainless steel in order to have a good chemical resistance at the time of cleaning the biopsy forceps 10. The base material may be made of martensitic stainless steel or other material such as brass and iron if the material can be processed an electroless nickel plating process. The chemical resistance is improved greatly if austenitic stainless steel is selected to be the base material.

Figure 4:
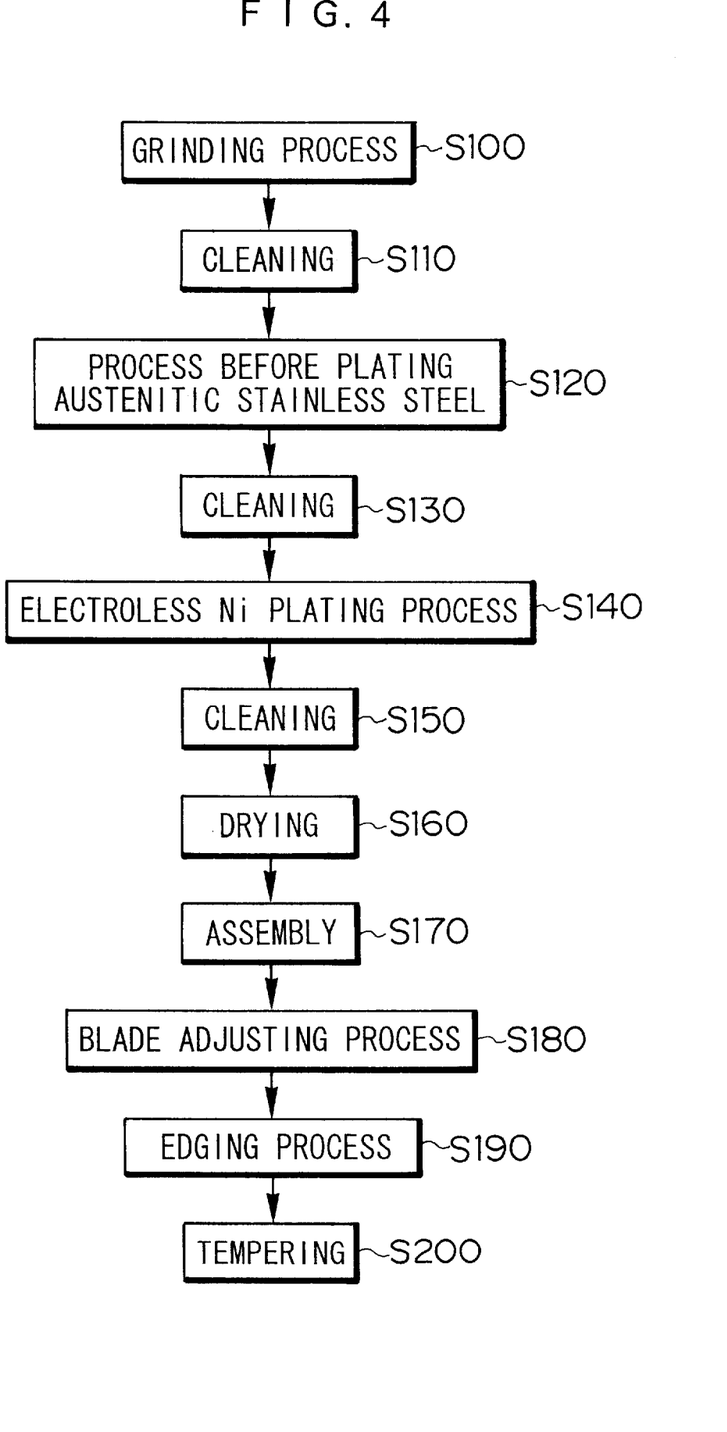
FIG. 4 is a flowchart showing a manufacturing process of the forceps piece.
Figure 5:
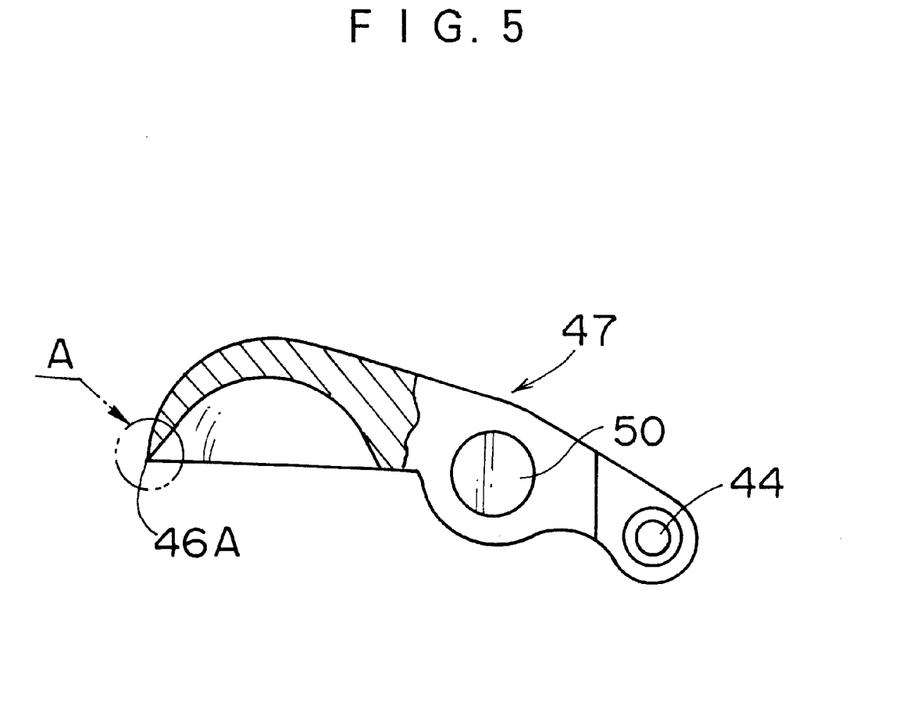
FIG. 5 is an enlarged section view showing essential parts of the forceps piece.

FIG. 4 is a flowchart showing a manufacturing process of the forceps piece. A piece of austenitic stainless steel is ground with a grinding tool to be shaped as a base material 47 shown in FIG. 5 (S100). At that time, a part that is supposed to be a blade of the forceps piece 46 does not have to be sharpened yet.

Then, the forceps piece base material 47 is cleaned (S110), and a preprocess such as electrolytic degreasing is performed before plating (S120) and the surface of the forceps piece base material 47 is activated.

Figure 6:
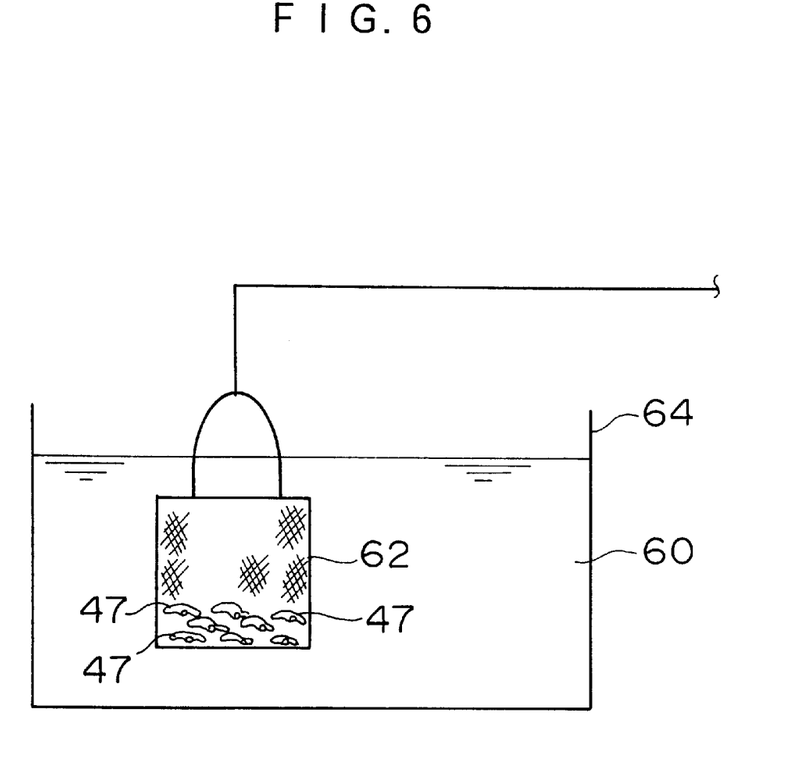
FIG. 6 is an explanatory view of an electroless plating process method for the forceps piece.
Figure 7:
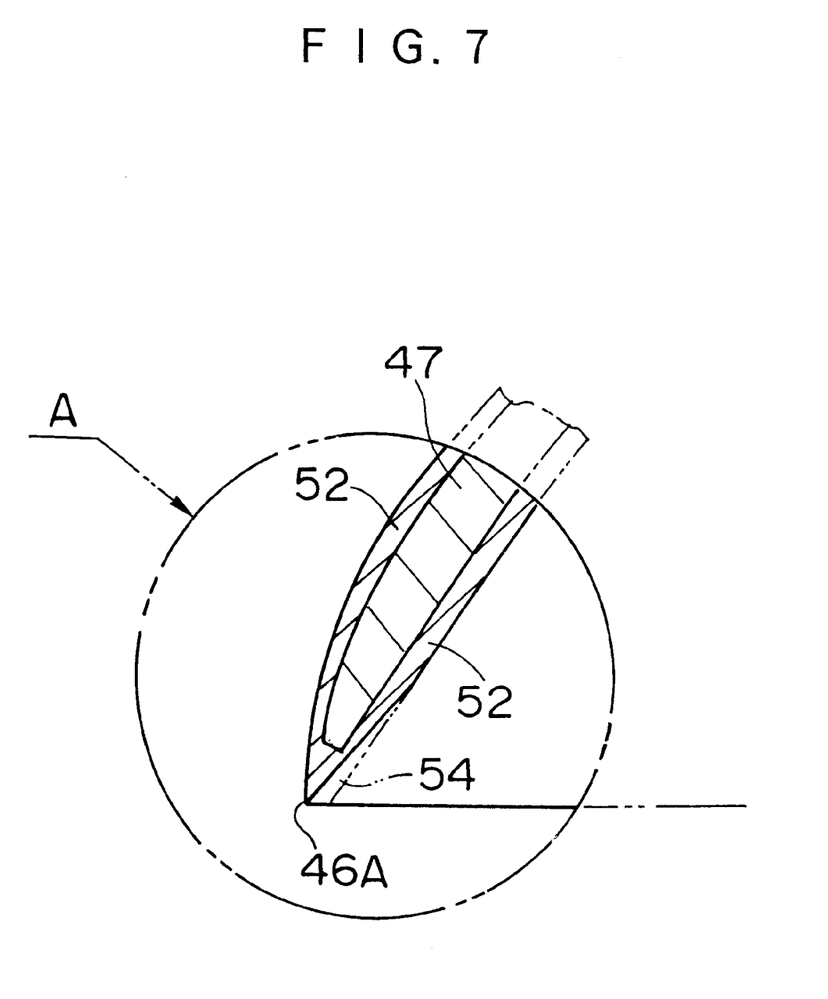
FIG. 7 is an enlarged section view of a blade part of the forceps piece.

The forceps piece base material 47 with the activated surface is cleaned (S130), then the base material 47 is immersed in electroless nickel plating process liquid 60 at a temperature of 90±5° C. as shown in FIG. 6, so as to perform an electroless nickel plating process (S140). In this embodiment, number of forceps piece base materials 47 are held in a mesh basket 62 and the mesh basket containing the base materials is immersed in the process liquid 60 held in a vessel 64, whereby the electroless nickel plating process is performed in batch processing. By this procedure, an electroless nickel plating film layer 52 is formed over the surface of the forceps piece base material 47 as shown in FIG. 7 by a reducing reaction. In this method, formalin, hypophosphorous acid, sodium hydrogen boride, and so forth may be used as reducing agents. By a three minute immersion, the electroless nickel plating film layer 52 of approximately 1 μm thick is formed. In this embodiment, the forceps piece base material 47 is immersed in the process liquid for 150 minutes so as to form the electroless nickel plating film layer 52 of approximately 50 μm thick. By extending the immersing time, the electroless nickel plating film layer 52 of approximately 100 μm thick can be formed.

Next, the forceps piece base material 47 on which the electroless nickel plating film layer 52 is formed is cleaned (S150) and is dried (S160), then the forceps piece base material 47 is assembled (S170) with another forceps piece base material of the forceps piece 48, which is manufactured by the same manufacturing process. Then, blade matching process (S180) is performed using a grindstone and the like. In other words, the top and bottom, and the right and left parts of both forceps piece base material are ground by the grindstone and the like so as to adjust the top, bottom, right, and left ends of both forceps piece base material.

Then, a thick part 54 of the electroless nickel plating film layer 52, which is shown with an alternate long and two short dashes line in FIG. 7, is sharpened to have an edge (S190), so that a sharp blade part 46A is formed. The same sharpening process is performed on the forceps piece base material of the forceps piece 48. By the above-described process, the forceps pieces 46 and 48 shown in FIGS. 2 and 3 are manufactured. Hardness of the blade part 46A at that time is approximately Hv500 (Hv: hardness value of Vickers). The hardness can be improved to approximately Hv700–800 by tempering the forceps pieces 46 and 48 (S200) after the edging process (S190) is completed.

As described above, since the electroless nickel plating film layer 52 is formed over the surface of the forceps piece base material 47, the forceps pieces 46 and 48 of the present embodiment can achieve good chemical resistance. Moreover, the electroless nickel plating film layer 52 displays hardness suitable for the forceps piece as well as superior toughness; thus the electroless nickel plating film layer can have an edge put on more easily than a hardened steel that has the same hardness, by edging the electroless nickel plating film layer. Therefore, good sharpness can be achieved.

Moreover, in the present embodiment, thickness of the electroless nickel plating film layer 52 is approximately between 50–100 µm. Thus, the edging process (S190) including the blade adjusting process (S180) can be easily done even though the cup-shaped blade parts have a poor engagement. Moreover, re-edging process can be easily performed even in a case where a blade is broken by an external force or where an error in a processed size is corrected; thus, the maintenance for the forceps improves.

In the present embodiment, the biopsy forceps 10 is exemplified as the forceps for the endoscope; but the forceps is not limited only to that. The present invention can be applied also to other forceps for an endoscope with a blade such as a scissors forceps.

Further, in the present embodiment, the electroless nickel plating film layer 52 is formed by use of process liquid of nickel salt; however the process liquid is not limited only to that. For example, the forceps piece can be provided with improved abrasion resistant, lubricity and hardness if the plating process is performed with a process liquid composed of nickel salt and phosphite including polytetrafluoroethylene and boron.

As has been described above, according to the forceps for the endoscope and the method for manufacturing the forceps of the present invention, the electroless nickel plating film layer is formed over the surface of the forceps piece base material, thus the forceps has a good chemical resistance. Moreover, since the electroless nickel plating film layer displays hardness suitable for the forceps piece as well as superior toughness, the edge can be put on the electroless nickel plating film layer. Furthermore, by applying the electroless nickel plating film layer as a thin film, re-edging can be easily performed even in a case where the blade is broken by an external force or where an error in a processed size is corrected; thus the maintenance for the forceps improves. The base material for the forceps piece is preferably made of austenitic stainless steel, so that the chemical resistance improves greatly.

It should be understood, however, that there is no intention to limit the invention to the specific forms disclosed, but on the contrary, the invention is to cover all modifications, alternate constructions and equivalents falling within the spirit and scope of the invention as expressed in the appended claims.

What is claimed is:

1. A method to manufacture a forcep for an endoscope, comprising:
   grinding and shaping a base material as a base for said forcep;
   electrolytic degreasing said base;
   nickel plating said base such that a thickness of a nickel plating film is in a specified range;
   assembling said base with another base; and
   sharpening at least one of said base and said another base, both of which said nickel plating film has been coated.

2. The method claim 1, wherein a thickness of said nickel plating film substantially ranges between 50 µm and 100 µm.

3. The method claim 1, wherein an electroless nickel plating process is used in said nickel plating step.

4. The method claim 3, wherein said an electroless nickel plating process is performed within a specified temperature range.

5. The method claim 4, wherein said temperature range is substantially between 85° C. and 95° C.

6. The method claim 7, electroless nickel plating process is performed at a temperature substantially at 90° C.

7. The method claim 3, wherein a processing liquid is used in said electroless nickel plating process.

8. The method of claim 7, wherein said processing liquid includes at least one of formalin, hypophosphorous acid, and sodium hydrogen boride as reducing agents.

9. The method of claim 1, wherein said another base is formed in a substantially same manner as said base.

10. The method of claim 1, wherein said sharpening is performed on said base and said another base wherein said base and said another base meet.

11. The method of claim 1, further comprising at least one of:
    cleaning said base after performing said grinding step;
    cleaning said base after performing said electrolytic degreasing step;
    cleaning and drying said base after performing said nickel plating step; and
    tempering said base and said another base after performing said sharpening step.

12. The method of claim 1, wherein said base material at least one of an austenitic stainless steel and a martensitic steel.

* * * * *